US012773168B2

(12) United States Patent
Stephenson

(10) Patent No.: US 12,773,168 B2
(45) **Date of Patent: *Oct. 27, 2026**

(54) EAR GEL MODULES AND EARPIECE MONITORING DEVICES INCORPORATING SAME

(71) Applicant: YUKKA MAGIC LLC, Wilmington, DE (US)

(72) Inventor: Shawn M. Stephenson, Raleigh, NC (US)

(73) Assignee: Yukka Magic LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/808,550

(22) Filed: Aug. 19, 2024

(65) Prior Publication Data

US 2024/0407731 A1 Dec. 12, 2024

Related U.S. Application Data

(63) Continuation of application No. 16/964,941, filed as application No. PCT/US2019/018252 on Feb. 15, 2019, now Pat. No. 12,082,946.

(60) Provisional application No. 62/632,686, filed on Feb. 20, 2018.

(51) Int. Cl.

| | |
|---|---|
| ***A61B 5/00*** | (2006.01) |
| ***G02B 6/42*** | (2006.01) |
| ***H04R 1/10*** | (2026.01) |

(52) U.S. Cl.

CPC .......... *A61B 5/7207* (2013.01); *A61B 5/0059* (2013.01); *A61B 5/6817* (2013.01); *G02B 6/4202* (2013.01); *H04R 1/1016* (2013.01); *A61B 2562/0233* (2013.01); *A61B 2562/185* (2013.01)

(58) Field of Classification Search

CPC .......... A61B 5/0059; A61B 2562/0233; A61B 5/02427; A61B 5/6817; G02B 6/4202; H04R 1/1016

See application file for complete search history.

(56) References Cited

U.S. PATENT DOCUMENTS 4,712,858 A 12/1987 Presby
4,783,137 A * 11/1988 Kosman ................. G02B 6/403 385/91
5,369,721 A 11/1994 Conti
(Continued)

FOREIGN PATENT DOCUMENTS

WO WO 2016/140835 9/2016
WO WO 2017/203251 11/2017

*Primary Examiner* — Oommen Jacob

(74) *Attorney, Agent, or Firm* — Brownstein Hyatt Farber Schreck, LLP

(57) ABSTRACT

An ear gel module for an earpiece includes an ear gel having opposite inner and outer surfaces and first and second light guides each having respective opposite first and second ends. The first end of the first light guide is secured to the inner surface of the ear gel, and the first end of the second light guide is secured to the inner surface of the ear gel in adjacent spaced-apart relationship with the third light guide first end. The second ends of the first and second light guides are configured to be attached to and in optical communication with respective light guides extending from a sensor module within the earpiece when the ear gel module is attached to the earpiece.

10 Claims, 10 Drawing Sheets

(56) References Cited

U.S. PATENT DOCUMENTS

| | | | | |
|---|---|---|---|---|
| 5,674,181 | A | 10/1997 | Lida | |
| 7,998,080 | B2 * | 8/2011 | Ben-Ari | A61B 5/0535 600/506 |
| 9,398,365 | B2 | 7/2016 | Liu | |
| 10,856,749 | B2 | 12/2020 | Just | |
| 10,973,415 | B2 | 4/2021 | LeBoeuf | |
| 11,324,407 | B2 | 5/2022 | LeBoeuf | |
| 12,082,946 | B2 * | 9/2024 | Stephenson | A61B 5/0059 |
| 2001/0034253 | A1 | 10/2001 | Ruschin | |
| 2005/0209516 | A1 | 9/2005 | Fraden | |
| 2012/0065343 | A1 | 3/2012 | Bahadur et al. | |
| 2013/0336495 | A1 | 12/2013 | Burgett et al. | |
| 2014/0249381 | A1 * | 9/2014 | LeBoeuf | A61B 5/0261 600/301 |
| 2016/0287108 | A1 | 10/2016 | Wei et al. | |
| 2017/0209095 | A1 | 7/2017 | Wagner et al. | |
| 2019/0029593 | A1 | 1/2019 | Orron | |
| 2021/0038161 | A1 | 2/2021 | Stephenson | |

* cited by examiner

EAR GEL MODULES AND EARPIECE MONITORING DEVICES INCORPORATING SAME

RELATED APPLICATION

This application is a continuation of U.S. patent application Ser. No. 16/964,941, filed Jul. 24, 2020, which is a National Phase Patent Application under 35 U.S.C. § 371 of International Application No. PCT/US2019/018252, filed Feb. 15, 2019, which claims the benefit of and priority to U.S. Provisional Patent Application No. 62/632,686 filed Feb. 20, 2018, which are hereby incorporated by reference in their entirety.

FIELD OF THE INVENTION

The present invention relates generally to monitoring devices and, more particularly, to optical sensor devices.

BACKGROUND OF THE INVENTION

There is growing market demand for personal health and environmental monitors, for example, for gauging overall health and metabolism during exercise, athletic training, dieting, daily life activities, sickness, and physical therapy. However, traditional health monitors and environmental monitors may be bulky, rigid, and uncomfortable—generally not suitable for use during daily physical activity.

Sensors for detecting biometric signals, such as vital signs and other physiological information, are configured to isolate the biometric signals from other spurious signals and deliver biometric readings, such as heart rate, respiration rate, blood pressure, etc., to the user. Unfortunately, spurious signals that may be difficult to isolate from a biometric signal are associated with physical movement (e.g., physical exercise, such as walking, running, daily activities, etc.) of a sensor relative to the user or the environment of the user (e.g., sunlight, room light, humidity, ambient acoustical or electromagnetic noise, temperature extremes or changes in temperature, etc.).

Previous ways of isolating heart rate signals from other signals include the use of passive and active signal processing algorithms, increasing optical sensor output and displacing the optical source from the photodetector, and pushing the sensor more firmly against the user so as to limit the effects of physical movement on the heart rate signal.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a biometric monitoring device that reduces the effects of motion includes a housing, an optical sensor module within the housing that is configured to detect and/or measure physiological information from a subject wearing the device, and an ear gel module secured to the housing. The optical sensor module includes an optical source and an optical detector. In some embodiments, multiple optical sources and/or optical detectors may be utilized. In some embodiments, at least one signal processor is located within the housing and is configured to process signals produced by the optical detector. The housing may further include a speaker driver configured to deliver sound to the subject wearing the device, for example from a portable device. In some embodiments, the optical sensor module may be secured directly to the speaker driver and may be electrically connected directly to the speaker driver.

A first light guide extends from the housing and has opposite first and second ends. The first end of the first light guide is in optical communication with the optical source, and the second end of the first light guide is located external to the housing. A second light guide extends from the housing and has opposite first and second ends. In some embodiments, the first light guide and/or the second light guide are supported by the housing. The first end of the second light guide is in optical communication with the optical detector, and the second end of the second light guide is located external to the housing. The second ends of the first and second light guides may be located external to the housing in adjacent spaced-apart relationship. The first and second light guides may be substantially rigid and comprise optically transmissive material, for example, material having a durometer measurement of between about Shore A40 and about Shore D100.

The ear gel module includes a body configured to interlock with or otherwise be secured, for example, removably secured, to a portion of the housing, a sound output tube, an ear gel, and a pair of third and fourth flexible light guides. The ear gel module may also include a stabilizing member that is configured to engage a conchal wall of the ear. The sound output tube has a free end with an opening, and the ear gel is attached to the sound output tube free end such that the ear gel extends around a portion of the sound output tube in coaxial relationship therewith. The ear gel includes opposite inner and outer surfaces. In some embodiments, the ear gel has a frusto-conical shape; however, various other shapes may be utilized.

The third light guide has opposite first and second ends, and the first end of the third light guide is secured to or is integrally formed with the inner surface of the ear gel. The fourth light guide has opposite first and second ends, and the first end of the fourth light guide is secured to or is integrally formed with the inner surface of the ear gel in adjacent spaced-apart relationship with the third light guide first end. The second end of the third light guide is attached to and is in optical communication with the second end of the first light guide. The second end of the fourth light guide is attached to and is in optical communication with the second end of the second light guide. The first and third light guides define a light path configured to deliver light from the optical source into a region of an ear of the subject wearing the device, and the second and fourth light guides define a light path configured to collect light from an ear region and deliver collected light to the optical detector. The ear gel and the third and fourth light guides comprise a flexible optically transmissive material, for example, material having a durometer measurement of between about Shore OO10 and about Shore A80.

When the monitoring device is worn by the subject, the ear gel is configured to be positioned at the auditory canal of the ear and thereby substantially limits any motion of the device 100 to rotational motion. In addition, in some embodiments, the first ends of the third and fourth light guides are positioned at a region of the ear between the tragus and the auditory canal.

In some embodiments, a divider is positioned between the third and fourth light guides and is configured to prevent or reduce light from crossing between the third and fourth light guides. In other embodiments, the divider may comprise translucent material that allows light to propagate between the third and fourth light guides. In other embodiments, the divider may be configured so as to serve as a wedge against the ear of a person wearing the monitoring device, thereby improving the fit and optical coupling of the ear gel.

In some embodiments, the ear gel module is configured to be removably secured to the housing such that the ear gel module is replaceable. The second end of the third light guide is removably attached to the second end of the first light guide, and the second end of the fourth light guide is removably attached to the second end of the second light guide. In some embodiments, the second end of the third light guide is telescopically engaged with the second end of the first light guide, and the second end of the fourth light guide is telescopically engaged with the second end of the second light guide.

According to other embodiments of the present invention, a biometric monitoring device that reduces the effects of motion includes a housing, an optical sensor module within the housing that is configured to detect and/or measure physiological information from a subject wearing the device, and an ear gel module secured to the housing. The optical sensor module includes an optical source and an optical detector. In some embodiments, multiple optical sources and/or optical detectors may be utilized. In some embodiments at least one signal processor is located within the housing and is configured to process signals produced by the optical detector. The housing may further include a speaker driver configured to deliver sound to the subject wearing the device, for example from a portable device. In some embodiments, the optical sensor module may be secured directly to the speaker driver and may be electrically connected directly to the speaker driver.

A first light guide extends from the housing and has opposite first and second ends. The first end of the first light guide is in optical communication with the optical source, and the second end of the first light guide is located external to the housing. A second light guide extends from the housing and has opposite first and second ends. The first end of the second light guide is in optical communication with the optical detector, and the second end of the second light guide is located external to the housing. In some embodiments, the first light guide and/or the second light guide are supported by the housing. The second ends of the first and second light guides may be located external to the housing in adjacent spaced-apart relationship. The first and second light guides may be substantially rigid and comprise optically transmissive material, for example, material having a durometer measurement of between about Shore A40 and about Shore D100.

The ear gel module includes a body configured to interlock with or otherwise be secured, for example, removably secured, to a portion of the housing, an ear gel, and a pair of third and fourth flexible light guides. The ear gel module may also include a stabilizing member that is configured to engage a conchal wall of the ear. The ear gel has opposite inner and outer surfaces. In some embodiments, the ear gel has a frusto-conical shape; however, various other shapes may be utilized.

The third light guide has opposite first and second ends, and the first end of the third light guide is secured to or is integrally formed with the inner surface of the ear gel. The fourth light guide has opposite first and second ends, and the first end of the fourth light guide is secured to or is integrally formed with the inner surface of the ear gel in adjacent spaced-apart relationship with the third light guide first end. The second end of the third light guide is attached to and is in optical communication with the second end of the first light guide. The second end of the fourth light guide is attached to and is in optical communication with the second end of the second light guide. The first and third light guides define a light path configured to deliver light from the optical source into a region of an ear of the subject wearing the device, and the second and fourth light guides define a light path configured to collect light from an ear region and deliver collected light to the optical detector. The ear gel and the third and fourth light guides comprise a flexible optically transmissive material, for example, material having a durometer measurement of between about Shore OO10 and about Shore A80.

When the monitoring device is worn by the subject, the ear gel is configured to be positioned at the auditory canal of the ear and thereby substantially limit any motion of the device to rotational motion. In addition, in some embodiments, the first ends of the third and fourth light guides are positioned at a region of the ear between the tragus and the auditory canal.

In some embodiments, a divider is positioned between the third and fourth light guides and is configured to prevent or reduce light from crossing between the third and fourth light guides. In other embodiments, the divider may comprise translucent material that allows light to propagate between the third and fourth light guides. In some embodiments, the divider may be configured so as to serve as a wedge against the ear of a person wearing the monitoring device, thereby improving the fit and optical coupling of the ear gel.

In some embodiments, the ear gel module is configured to be removably secured to the housing such that the ear gel module is replaceable. The second end of the third light guide is removably attached to the second end of the first light guide, and the second end of the fourth light guide is removably attached to the second end of the second light guide. In some embodiments, the second end of the third light guide is telescopically engaged with the second end of the first light guide, and the second end of the fourth light guide is telescopically engaged with the second end of the second light guide.

According to other embodiments of the present invention, a replaceable ear gel module for an earpiece includes a body configured to interlock with or otherwise be secured, for example, removably secured, to a portion of an earpiece housing, an ear gel, and a pair of first and second flexible light guides. The ear gel module may also include a stabilizing member that is configured to engage a conchal wall of an ear. The ear gel has opposite inner and outer surfaces. In some embodiments, the ear gel has a frusto-conical shape; however, various other shapes may be utilized.

The first light guide has opposite first and second ends, and the first end of the first light guide is secured to or is integrally formed with the inner surface of the ear gel. The second light guide has opposite first and second ends, and the first end of the second light guide is secured to or is integrally formed with the inner surface of the ear gel in adjacent spaced-apart relationship with the third light guide first end. The second ends of the first and second light guides are configured to be attached to and in optical communication with respective light guides extending from a sensor module within an earpiece housing when the ear gel module is attached to the earpiece. The ear gel and the first and second light guides comprise a flexible optically transmissive material, for example, material having a durometer measurement of between Shore OO10 and Shore A80.

In some embodiments, a divider is positioned between the first and second light guides and is configured to prevent or reduce light from crossing between the first and second light guides. In other embodiments, the divider may comprise translucent material that allows light to propagate between the first and second light guides. In some embodiments, the divider may be configured so as to serve as a wedge against the ear of a person wearing the monitoring device, thereby improving the fit and optical coupling of the ear gel.

In some embodiments, the ear gel module is configured to be removably secured to the housing of an earpiece such that the ear gel module is replaceable.

According to other embodiments of the present invention, a replaceable ear gel module for an earpiece includes a body configured to interlock with or otherwise be secured, for example removably secured, to a portion of an earpiece housing, a sound output tube, an ear gel, and a pair of first and second flexible light guides. The ear gel module may also include a stabilizing member that is configured to engage a conchal wall of an ear. The sound output tube has a free end with an opening, and the ear gel is attached to the sound output tube free end such that the ear gel extends around a portion of the sound output tube in coaxial relationship therewith. The ear gel includes opposite inner and outer surfaces. In some embodiments, the ear gel has a frusto-conical shape; however, various other shapes may be utilized.

The first light guide has opposite first and second ends, and the first end of the first light guide is secured to or is integrally formed with the inner surface of the ear gel. The second light guide has opposite first and second ends, and the first end of the second light guide is secured to or is integrally formed with the inner surface of the ear gel in adjacent spaced-apart relationship with the third light guide first end. The second ends of the first and second light guides are configured to be attached to and in optical communication with respective light guides extending from a sensor module within an earpiece housing when the ear gel module is attached to the earpiece. The ear gel and the first and second light guides comprise a flexible optically transmissive material, for example, material having a durometer measurement of between Shore OO10 and Shore A80.

In some embodiments, a divider is positioned between the first and second light guides and is configured to prevent or reduce light from crossing between the first and second light guides. In other embodiments, the divider may comprise translucent material that allows light to propagate between the first and second light guides. In some embodiments, the divider may be configured so as to serve as a wedge against the ear of a person wearing the monitoring device, thereby improving the fit and optical coupling of the ear gel.

In some embodiments, the ear gel module is configured to be removably secured to the housing of an earpiece such that the ear gel module is replaceable.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIG. 1A is a front view of a human ear, FIG. 1B is a side view thereof, and FIG. 1C is a back view thereof.

DETAILED DESCRIPTION

Figures 1A, 1B, 1C:
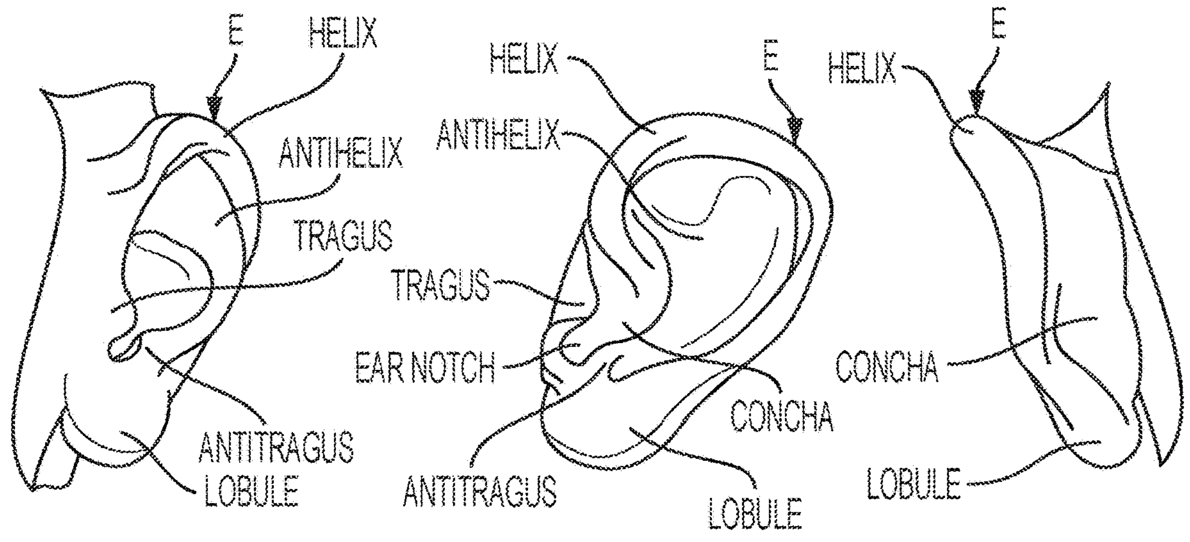
FIGS. 1A-1C illustrate the anatomy of the human ear.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled", or "secured" to another feature or element, it can be directly connected, attached, coupled, or secured to the other feature or element or intervening features or elements may be present. In contrast, when a feature or element is referred to as being "directly connected", "directly attached", "directly coupled", or "directly secured" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary, for example, by as much as +/−20%.

The term "earpiece", as used herein, is intended to include any type of device, including earbuds, headsets, hearing aids, etc., that may be attached to the ear (or ears) of a user and may have various configurations, without limitation.

The terms "optical source" and "optical emitter", as used herein, are interchangeable.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" may include monitoring blood gas levels, blood hydration, and metabolite/electrolyte levels, etc.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) that may wear a device incorporating one or more optical sensor modules, according to embodiments of the present invention.

The term "coupling", as used herein, refers to the interaction or communication between excitation light entering a region of a body and the region itself. For example, one form of optical coupling may be the interaction between excitation light generated from an optical sensor module and the blood vessels of the body of a user. In one embodiment, this interaction may involve excitation light entering the ear region and scattering from a blood vessel in the ear such that the intensity of scattered light is proportional to blood flow within the blood vessel.

The term "processor" is used broadly to refer to a signal processor or computing system or processing or computing method which may be localized or distributed. For example, a localized signal processor may comprise one or more signal processors or processing methods localized to a general location, such as to an earpiece. Examples of a distributed processor include "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. As a specific example, microprocessors, microcontrollers, ASICs (application specific integrated circuits), analog processing circuitry, or digital signal processors are a few non-limiting examples of physical signal processors that may be found in wearable devices.

The term "remote" does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. However, any wireless device (such as a portable device, for example) or system (such as a remote database for example) is considered remote to any other wireless device or system.

Figure 2:
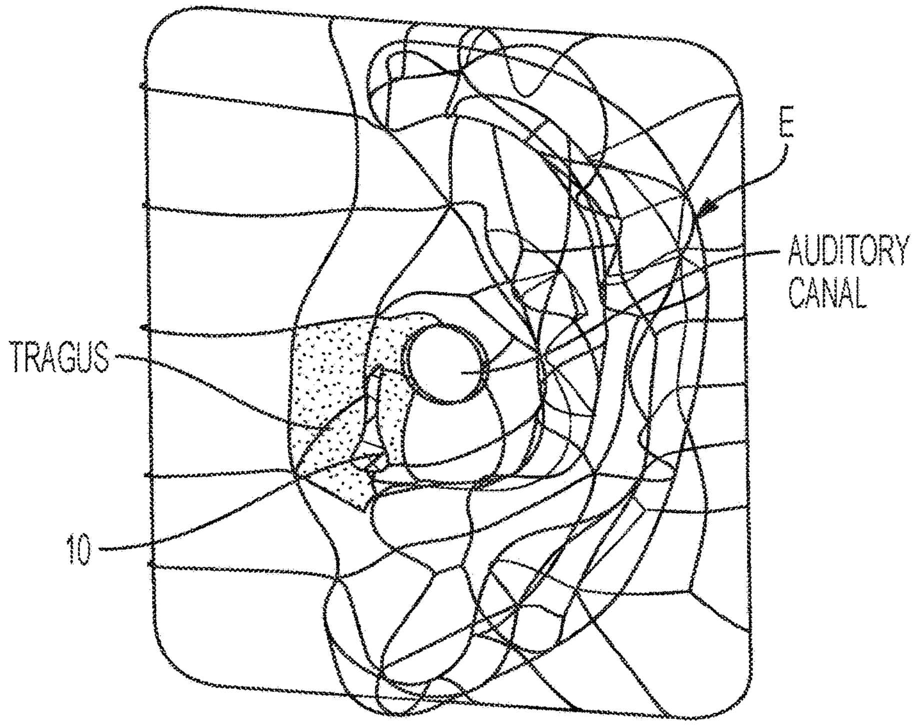
FIG. 2 illustrates a region of a human ear between the Tragus and the Auditory Canal from which physiological information can be obtained via biometric monitoring devices of the present invention.
Figure 3A:
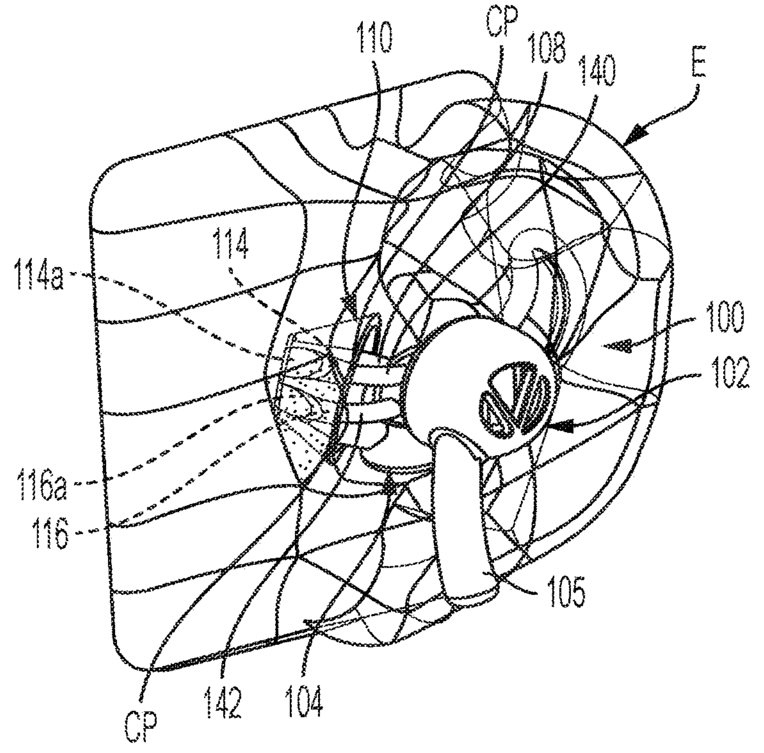
FIG. 3A illustrates a biometric monitoring device, according to some embodiments of the present invention, that is positioned within an ear and configured to obtain physiological information from the region between the Tragus and the Auditory Canal identified in FIG. 2.
Figure 3B:
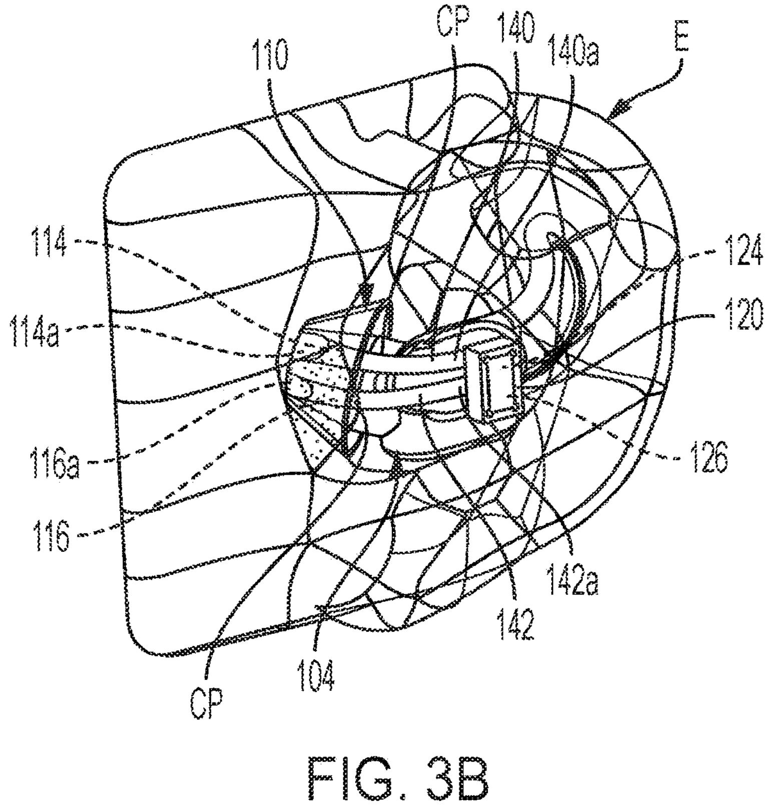
FIG. 3B illustrates the biometric monitoring device of FIG. 3A with the earpiece housing removed to reveal a sensor module and light guides extending from the sensor module.
Figure 5A:
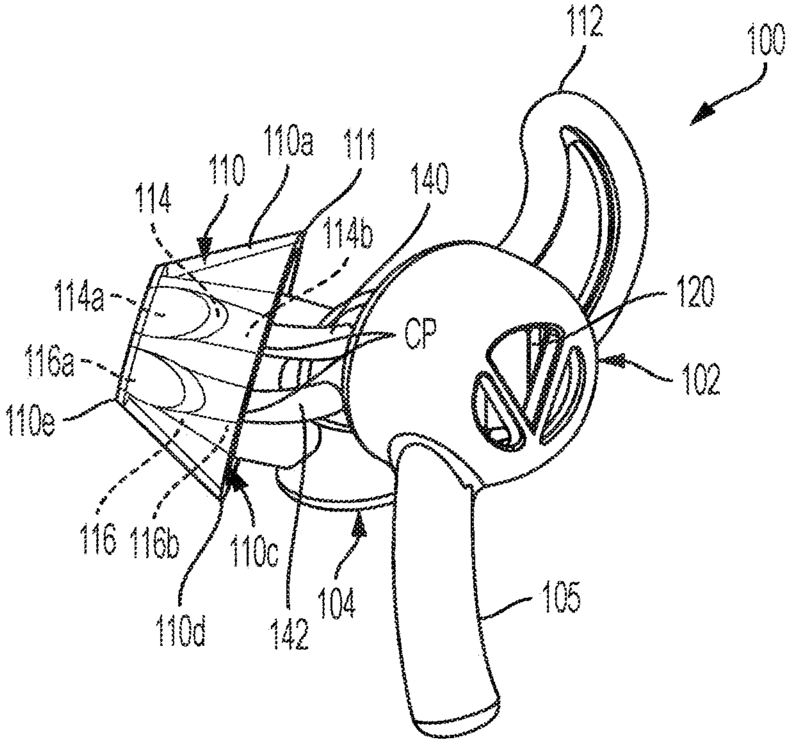
FIG. 5A is a perspective view of the biometric monitoring device of FIG. 3A.

FIGS. 1A-1C illustrate the anatomy of the human ear E. FIG. 1A is a front view of a human ear E, FIG. 1B is a side view thereof, and FIG. 1C is a back view thereof. Embodiments of the present invention enable obtaining physiological information from various regions of the ear, and particularly from a region (identified as 10 in FIG. 2) of a human ear between the Tragus and the Auditory Canal. For example, FIGS. 3A-3B and 5A illustrate an earpiece device 100 that is configured to obtain physiological information from the region 10 within an ear E that is between the Tragus and the Auditory Canal identified in FIG. 2. The illustrated device 100 includes a housing 102 and an ear gel module 104 that is removably secured to the housing 102. Enclosed within the housing 102 are a speaker driver (not shown) and a sensor module 120 (FIG. 3B). Various additional components may be enclosed within the housing 102, such as one or more signal processors, a power source, additional sensors/sensor modules, etc.

Figure 5B:
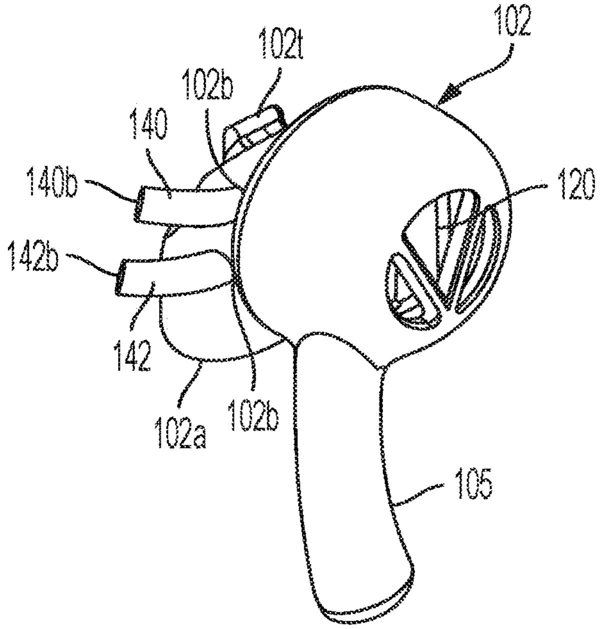
FIG. 5B illustrates the earpiece housing of the biometric monitoring device of FIG. 5A with the ear gel module removed.
Figure 5C:
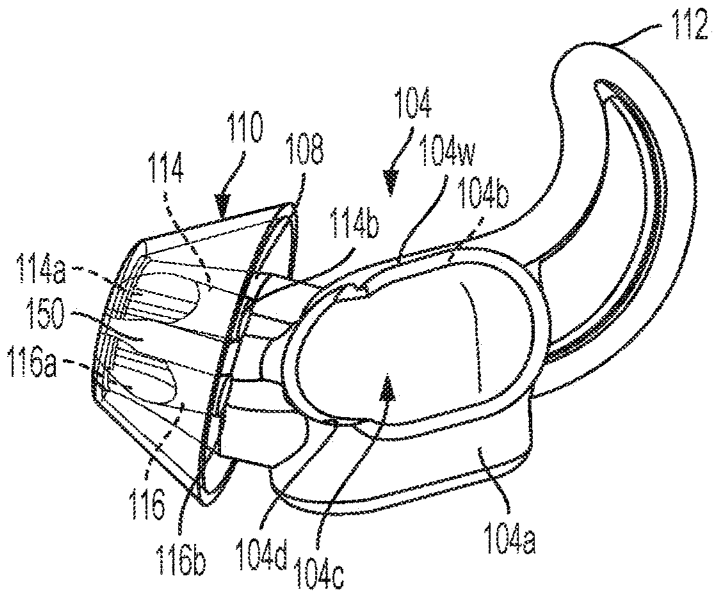
FIG. 5C illustrates the ear gel module of the biometric monitoring device of FIG. 5A. The ear gel module is configured to be removably secured to the earpiece housing shown in FIG. 5B. The internal components of the earpiece housing are removed for clarity.

The ear gel module 104 is designed to be replaceable and can be removably secured to the housing 102 in various ways. The replaceable ear gel module 104 has a geometry and configuration that interlocks with a corresponding geometry and configuration of the housing 102. For example, as illustrated in FIG. 5B, the housing includes a portion 102*a* that is configured to be inserted within a receiving portion or cavity 104*c* of a body 104*a* of the ear gel module 104 and also includes a protruding part or rib 102*t* that is configured to be inserted within a mating feature 104*b* formed in the interior surface of the ear gel module wall 104*w*. The mating feature 104*b* and the rib 102*t* can have various shapes and configurations and are not limited to the illustrated configuration. In some embodiments, the mating feature 104*b* can extend all the way through the ear gel module wall 104*w* such that the rib 102*t* or a portion thereof is visible. The interlocking geometry of the ear gel module 104 and housing 102 serve to constrain the ear gel module 104 to the housing 102, yet allow the ear gel module 104 to be removable.

Referring to FIG. 3B, the sensor module 120 includes an optical source 124 and an optical detector 126. FIG. 3B illustrates the earpiece housing removed to reveal the sensor module 120 contained therewithin and the light guides 140, 142 that extend from the sensor module 120. As would be understood by one skilled in the art of the present invention, the sensor module 120 and/or the device 100 may include various additional electronic components including, but not limited to, a signal processor, a wireless module for communicating with a remote device, a memory storage device, etc. Moreover, a battery, such as a lithium polymer battery or other portable battery, may be mounted to or connected to the sensor module 120, or otherwise located within the housing 102, and may be charged via a charge port, such as a USB charge port, for example. Alternatively, or in addition, a connection area to access an external power source via a port or through soldering, may be included within the housing 102.

Referring to FIG. 3A, the illustrated housing 102 also includes a shroud or hollow stem 105 through which one or more wires W can extend to provide sound to a speaker within the housing 102, for example from a portable device. The stem 105 may be formed from a rigid material or may be formed from a flexible material. However, in some embodiments, an earpiece with an ear gel module may be a wireless earpiece and no wires extend from the housing 102.

In some embodiments, the sensor module 120 may be secured to a speaker driver (not shown) within the housing 102 of the biometric monitoring device 100, for example, as described in U.S. Patent Application Publication No. 2017/0209095, which is incorporated herein by reference in its entirety.

The optical source 124 may be one or more light-emitting diodes (LED), laser diodes (LD), compact incandescent bulbs, micro-plasma emitters, IR blackbody sources, organic LEDs, or the like. The optical detector 126 may be one or more photodiodes, photodetectors, phototransistors, thyristors, solid state devices, optical chipsets, or the like.

As described further below, the illustrated ear gel module 104 has a generally frusto-conical shaped ear gel 110 that is configured to be positioned within the entrance to the Auditory Canal and to substantially eliminate any motion of the device 100 other than rotational motion. However, the ear gel 110 may have various other shapes. Embodiments of the present invention are not limited to the ear gel 110 having a frusto-conical shape. The illustrated ear gel 110 also includes conformable light guides molded thereto that are positioned at region 10 of FIG. 2 when the device 100 is worn in an ear E.

The Tragus area of the ear E is in proximity to the Auditory Canal, which is generally circular in shape. Obtaining physiological information from the sensing location 10 can reduce the influence of subject and monitoring device motion at the sensing location 10 because it is in close relationship to the Auditory Canal, which serves as an anchor point for the ear gel 110 of the biometric monitoring device 100.

Figure 4A:
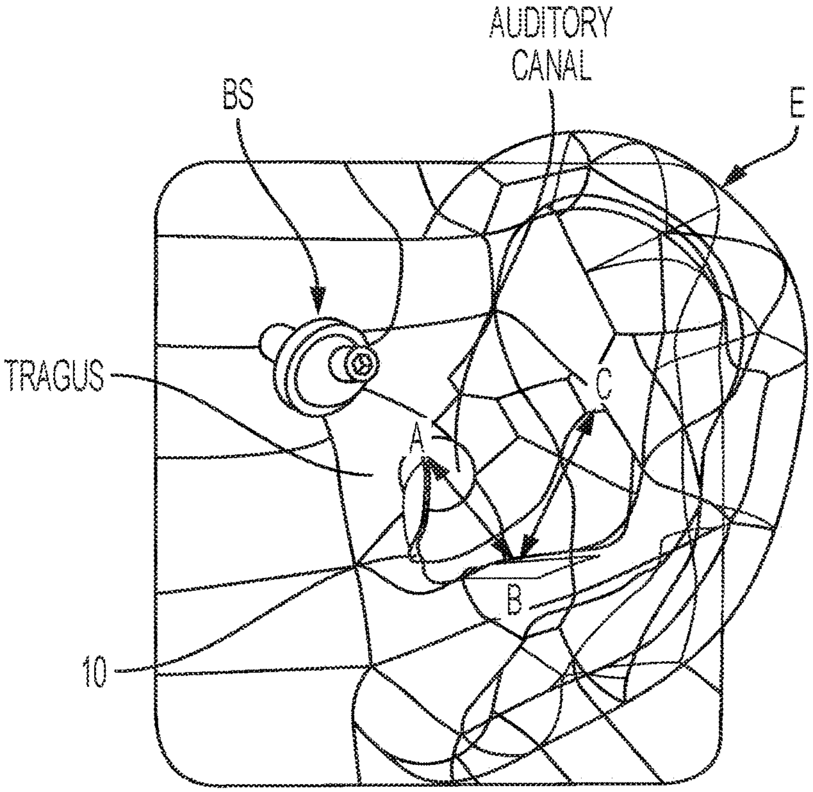
FIG. 4A illustrates force components experienced by the biometric monitoring device of FIG. 3A within the ear.

Referring to FIG. 4A, the configuration of the biometric monitoring device 100 causes contact with the ear at point A (entrance to Auditory Canal), point B (Concha), and at point C (location of the ear where the stabilizing member 112 makes contact). The force components A-B and C-B are reduced as a result of the primary movement of the biometric monitoring device 100 being rotation of the ear gel 110 at the Auditory Canal, thereby improving comfort to the person wearing the biometric monitoring device 100. The rotational engagement of the ear gel 110 with the entrance to the Auditory Canal makes it unnecessary to increase forces in other areas of the ear to maintain stability of the biometric monitoring device 100. Additionally, the force exerted by the entrance of the Auditory Canal on the ear gel 110 greatly stabilizes the sensing location, further reducing the noise caused by shifting of the ear gel 110 against the skin of the ear.

As shown in FIG. 4A, movement of the biometric monitoring device 100 at the Auditory Canal (referred to as point A in FIG. 4A) is primarily rotation, as represented by the ball and socket illustration BS. The socket is representative of the Auditory Canal and the ball is representative of the frusto-conical shaped ear gel 110 of the device 100. Little, if any, translation of the monitoring device 100 can occur here because of the ear gel 110 being pressed within the entrance of the Auditory Canal (i.e., at point A).

Figure 4B:
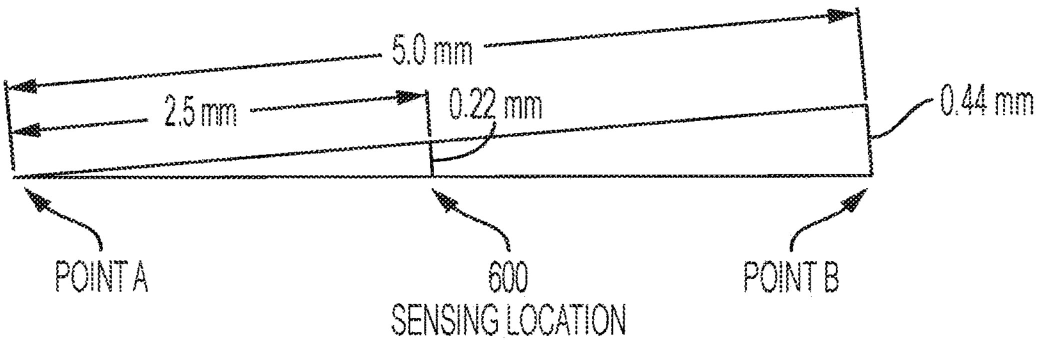
FIG. 4B illustrates the relationship between angular movement at point A in FIG. 4A and translation.

FIG. 4B illustrates that substantially the only movement of the monitoring device 100 at point A is rotational movement (i.e., rotational movement of the ear gel 110 relative to the entrance to the Auditory Canal). As the sensing location moves away from point A, any angular movement at point A allows for greater translation. For example, as shown in FIG. 4B, a five degree (5°) rotation of the device 100 when anchored at point A creates half the movement at a 2.5 mm distance from point A than at a 5.00 mm distance form point A.

Referring now to FIGS. 5A-5C and 6A-6C, the biometric monitoring device 100 is described further. The illustrated ear gel module 104 includes a sound output tube 108 that defines a passageway or port 108*p* configured to direct sound from a speaker within the earpiece housing 102 to the ear of a wearer of the device 100. The sound output tube 108 terminates at an opening 108*a* at a distal free end 108*b* thereof. The illustrated ear gel module 104 also includes an ear gel 110 and a stabilizer member 112. In the illustrated embodiment, the body 104*a* of the ear gel module 104 includes a cut away portion 104*d* that allows the ear gel module 104 to be attached to the housing 102 without interfering with the light guides 140, 142 extending outwardly from the housing 102.

The ear gel 110 is attached to the sound output tube free end 108*b* and extends around the sound output tube 108 in coaxial relationship therewith to form a circumferential space 110*c*, as illustrated. In some embodiments, the sound tube 108 and ear gel 110 are integrally formed as a unit, for example during molding operations. The ear gel 110 is formed of a soft, conformable material, such as silicone, and includes an outer surface 110*a* and an opposite inner surface 110*b*, and a circumferential free end 110*d* opposite of end 110*e* at the sound tube distal end 108*b*. The ear gel 110 may have a substantially uniform wall thickness between the outer surface 110*a* and the inner surface 110*b* from end 110*d* to end 110*e*. However, variable wall thicknesses may be utilized in some embodiments.

Figure 6A:
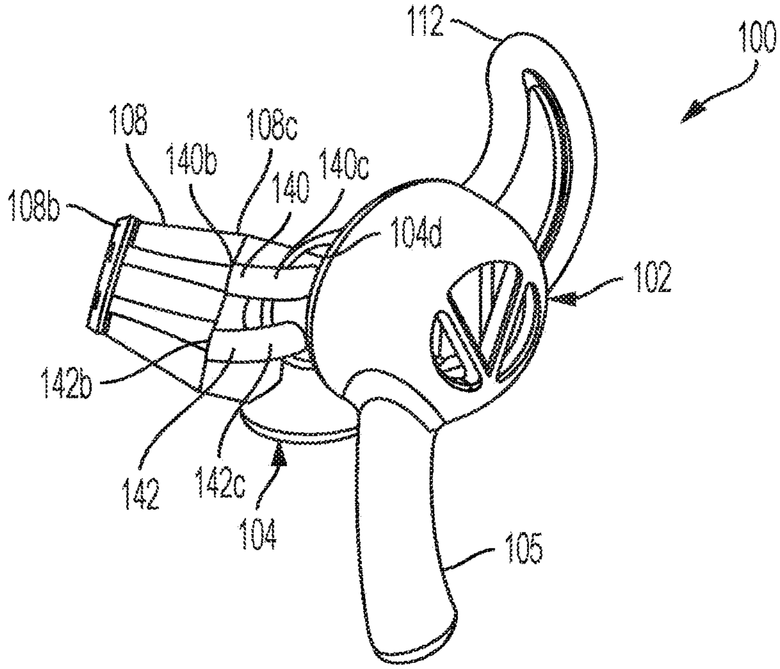
FIG. 6A is a perspective view of the biometric monitoring device of FIG. 5A with the ear gel removed from the ear gel module for clarity.
Figure 6B:
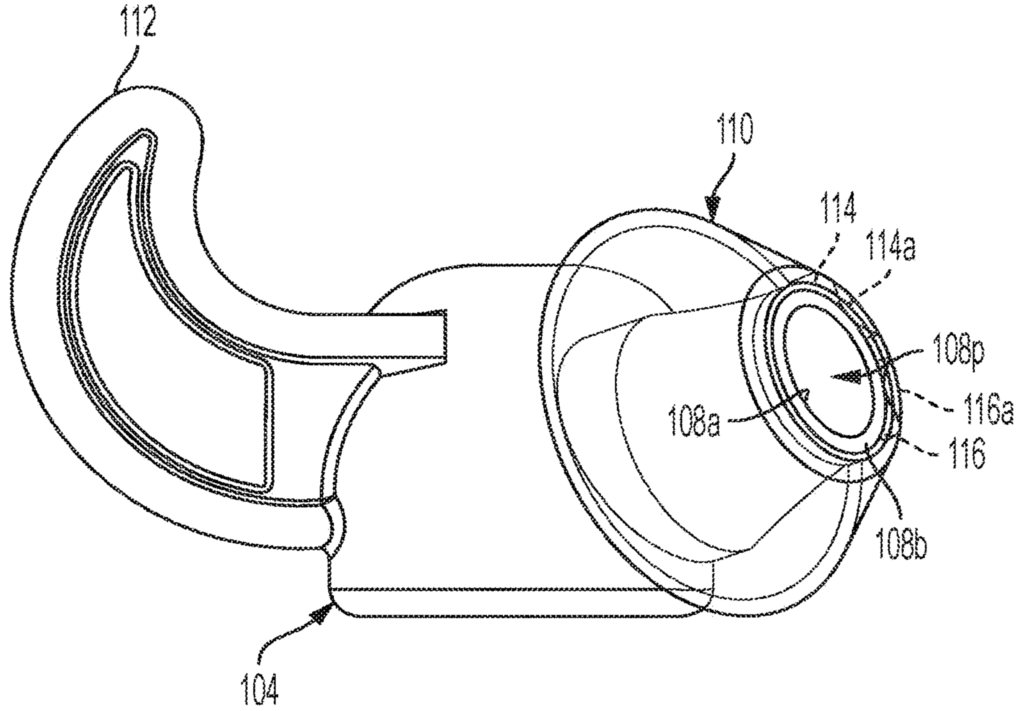
FIGS. 6B-6C are different perspective views of the ear gel module of the biometric monitoring device of FIG. 5A.
Figure 6C:
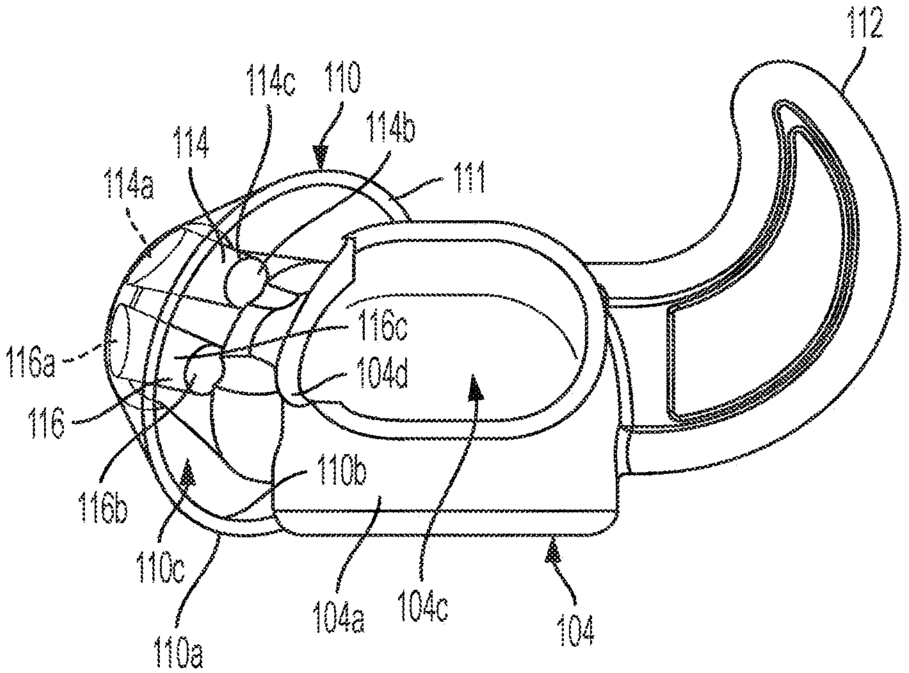

At the circumferential free end 110*d*, a diameter D1 (FIG. 7B) of the ear gel 110 is greatest. The diameter of the ear gel 110 decreases in the direction towards the sound port end 108*b* such that a diameter D2 of the ear gel 110 is the smallest at end 110*e*. The circumferential space 110*c* provides room for the flexible light guides 114, 116 (described below) that are secured to or integrally formed with the ear gel 110, as illustrated in FIG. 6C.

The ear gel module 104 is configured to be removably secured to the housing 102 such that a user can select and attach to the housing 102 an ear gel module 104 that best fits the ear of the user. Ear gel modules 104 can be provided with different size stabilizing arms 112 and different size ear gels 110. In some embodiments, a stabilizing arm may not be required. Embodiments of the present invention are not limited to ear gel modules having a stabilizing arm.

The illustrated ear gel 110 also includes a pair of flexible light guides 114, 116. The flexible light guides 114, 116 are attached to or integrally formed with the inner surface 110*b* of the ear gel 110 at respective ends 114*a*, 116*a*. In some embodiments, the light guides 114, 116 are molded with the ear gel 110 such that the ear gel 110 and the light guides 114, 116 are an integral unit. The flexible light guides 114, 116 are configured to be malleable with the ear gel 110 when the monitoring device 100 is secured to the ear. In other words, the flexible light guides 114, 116 are conformable with the ear gel 110 as the ear gel 110 is pressed into the entrance of the auditory canal of an ear. The flexible light guides 114, 116 are molded onto the inner surface 110*b* such that their ends 114*a*, 116*a* are exposed through the wall 111 of the ear gel 110. As such, the light guides 114, 116 can deliver and collect light via the respective ends 114*a*, 116*a* through the light transmissive ear gel wall 111.

In some embodiments of the present invention, the ear gel module 104 may include a divider 150 positioned between the flexible light guides 114, 116 that is configured to prevent or reduce light from crossing between the light transmission path and light receiving path. In other embodiments, the divider may be translucent, thereby allowing light to propagate between the flexible light guides 114, 116.

Figure 8A:
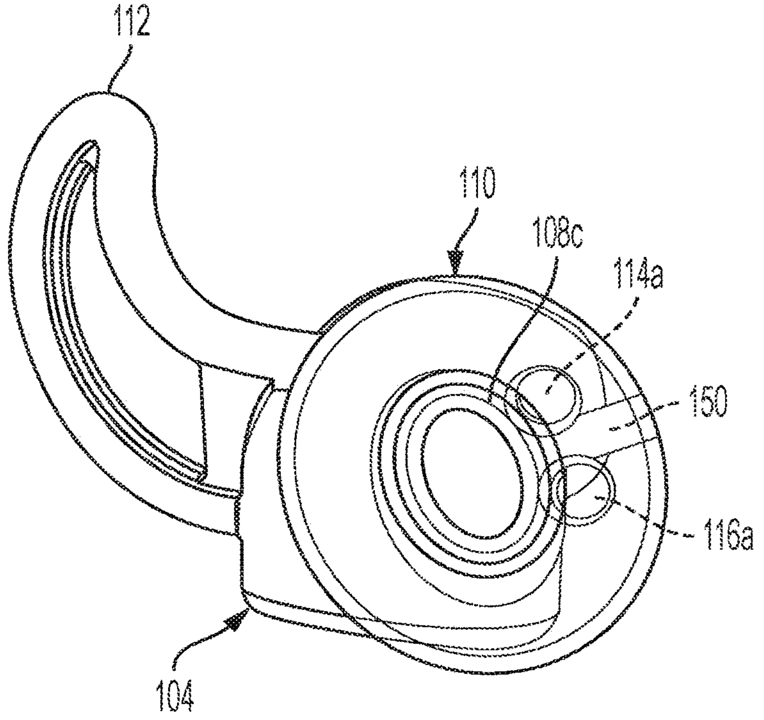
FIGS. 8A-8B illustrate an ear gel module having a divider positioned between the flexible light guides, according to some embodiments of the present invention.
Figure 8B:
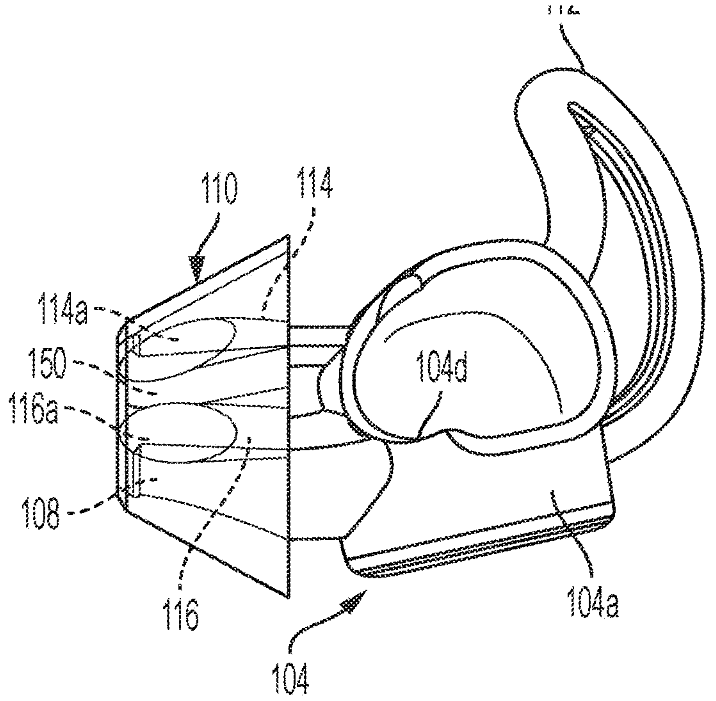

In some embodiments, the divider 150 is attached to the sound output tube 108 and extends from an outer surface 108*c* of the sound output tube 108 to the inner surface 110*b* of the ear gel 110, as illustrated in FIGS. 8A-8B. The divider 150 can be configured to abut the inner surface 110*b* of the ear gel 110 or could be attached to the inner surface 110*b* of the ear gel 110. In other embodiments, the divider 150 could be attached to the inner surface 110*b* of the ear gel 110 and extend to the outer surface 108*c* of the sound output tube 108. The divider 150 can be configured to abut the outer surface 108*c* of the sound output tube 108 or could be attached to the outer surface 108*c* of the sound output tube 108.

The divider 150 may be formed from a soft, conformable material. The divider 150 can also be formed from a more rigid material such that the divider serves as a wedge against the ear of a person wearing the device 100, thereby improving the fit/stability and, thus, the optical coupling of the ear gel 110.

Figure 9A:
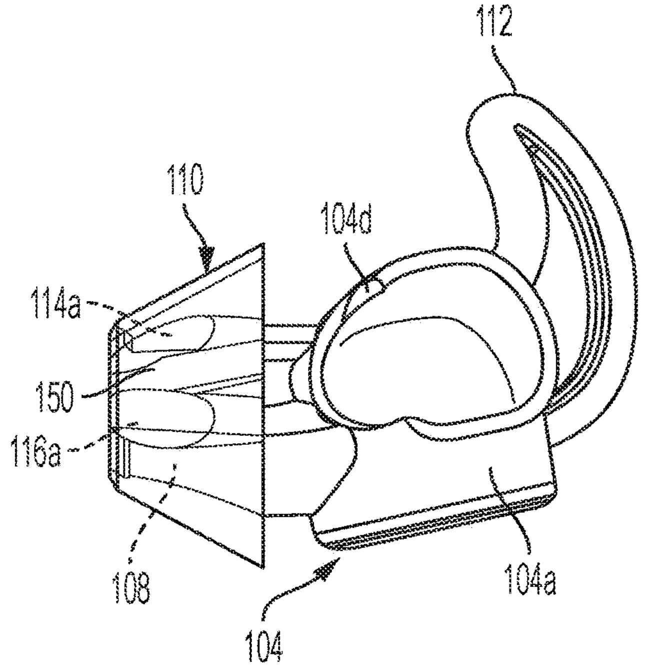
FIGS. 9A-9B illustrate an ear gel module having a divider positioned between the flexible light guides, according to some embodiments of the present invention.
Figure 9B:
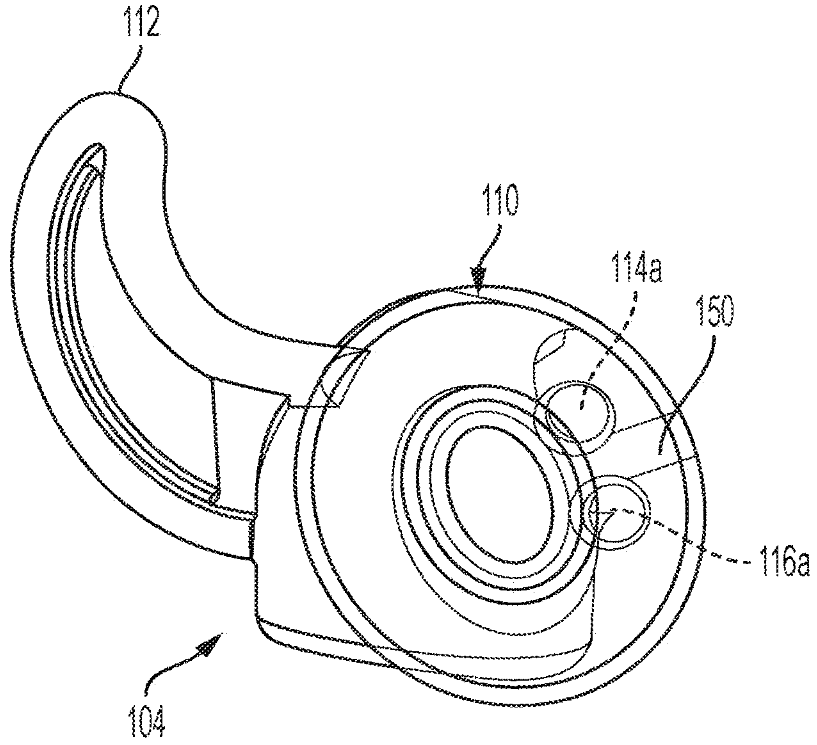

In the illustrated configuration of FIGS. 8A-8B, the flexible light guides 114, 116 are partially separated by the divider 150. When opaque, the divider 150 in this configuration allows some light to cross between the transmission path and receiving path though the ear gel 110. In other embodiments, the divider 150 can extend all the way to the outer surface 110*a* of the ear gel 110, as illustrated in FIGS. 9A-9B. For example, using a two-shot molding method, the divider 150, when desired to be formed of opaque material, would be produced with the first-shot and the light transmissive remaining portion of the ear gel 110 could be molded around the opaque divider 150, or vice-versa. In other embodiments, the ear gel 110 may include a slot configured to receive a portion of the divider 150. Various ways of providing a divider 150 between the two flexible light guides 114, 116 can be utilized.

Figure 7A:
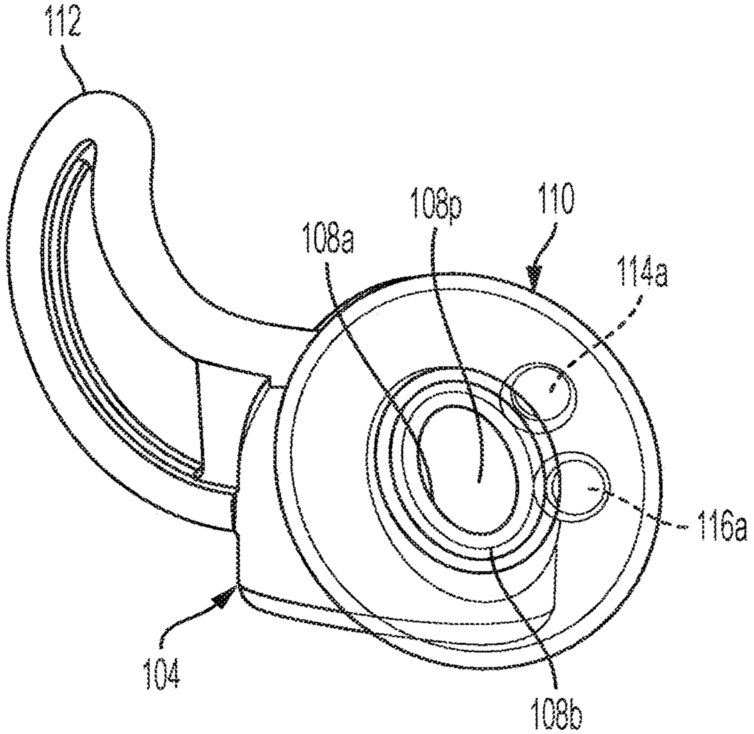
FIGS. 7A-7B illustrate an ear gel module, according to some embodiments of the present invention, wherein the flexible light guides attached to the ear gel are not separated by a divider.
Figure 7B:
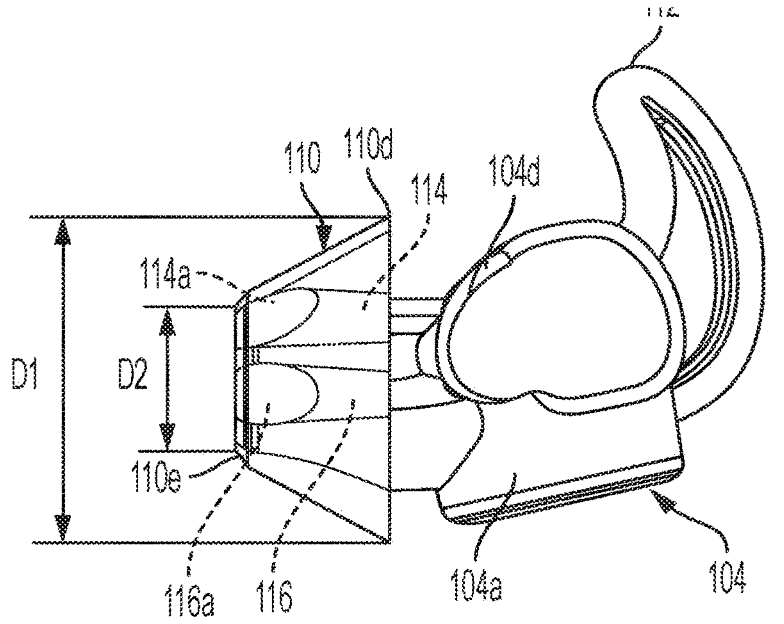

However, embodiments of the present invention are not limited to the presence of a divider between the flexible light guides 114, 116. For example, FIGS. 7A-7B illustrate an ear gel 110 wherein the flexible light guides 114, 116 are not separated by a divider.

In some embodiments of the present invention, all of the features of the ear gel module 104 (i.e., ear gel 110, stabilizer 112, and flexible light guides 114, 116) can be manufactured via a single-shot mold using silicone having the same durometer. Alternatively, the aforementioned features can have different durometer values, as a result of using different manufacturing methods and/or materials. Material for the ear gel module 104 is not limited to silicone; various other soft, thermoplastic elastomers that are light-transparent, may be used, also. In some embodiments, the ear gel 110 and the flexible light guides 114, 116 comprise a flexible optically transmissive material having a durometer measurement of between Shore OO10 and Shore A80. In some embodiments, the light guides 140, 142 comprise an optically transmissive rigid or less flexible material having a durometer measurement of between about Shore A40 and about Shore D100.

Improved optical coupling is achieved at the sensing location 10 (FIG. 2) because of the soft, conformable material of the ear gel 110 that increases in surface area when acted upon by the surrounding anatomy of the entrance to the Auditory Canal. For example, when the outer surface 110*a* of the ear gel rests 110 upon a planar surface, point contact exists. However, when the ear gel 110 is acted upon by the surrounding geometry of the ear (i.e., non-planar surface), the ear gel 110 deforms along with the ends 114*a*, 116*a* of the flexible light guides 114, 116 and point contact now adapts to mimic the area of the surrounding ear anatomy. Point contact, thus, increases to area contact. However, the dimensions of the flexible light guides 114, 116 attached to the ear gel 110 themselves are not greatly affected by motion and hence do not generate a significant amount of motion artifacts during physical activity of the user wearing the device 100.

The ends 114*a*, 116*a* of the light guides 114, 116 (as well as the light guides 114, 116 themselves) are soft and compliant such that a deformation (i.e., change of shape as a result of being inserted in an ear) of the ear gel 110 at the vicinity of the light guides 114, 116, causes the light guides 114, 116 to also deform, but without contributing to motion artifacts within light passing through the light guides 114, 116. The soft, compliant nature of the flexible light guides 114, 116 improves optical coupling at the sensing region 10 of the ear because of the reduced susceptibility to motion. For example, a portion of each flexible light guide 114, 116 within the ear gel 110 changes shape (i.e., deforms) with the ear gel 110 so as not to become optically decoupled from the sensing region 10 of the ear. The increased optical coupling, increases the desired modulated signal (the blood flow signal) in the total signal to noise ratio. It also serves to further reduce movement of the monitoring device 100 as the additional surface area increases friction.

The flexible light guides 114, 116 each include an opposite free end 114*b*, 116*b* that is configured to be optically and physically coupled to the free ends 140*b*, 142*b* of the light guides 140, 142 that extend from the sensor module 120 (FIG. 3B) within the housing 102, and described below.

Figure 3C:
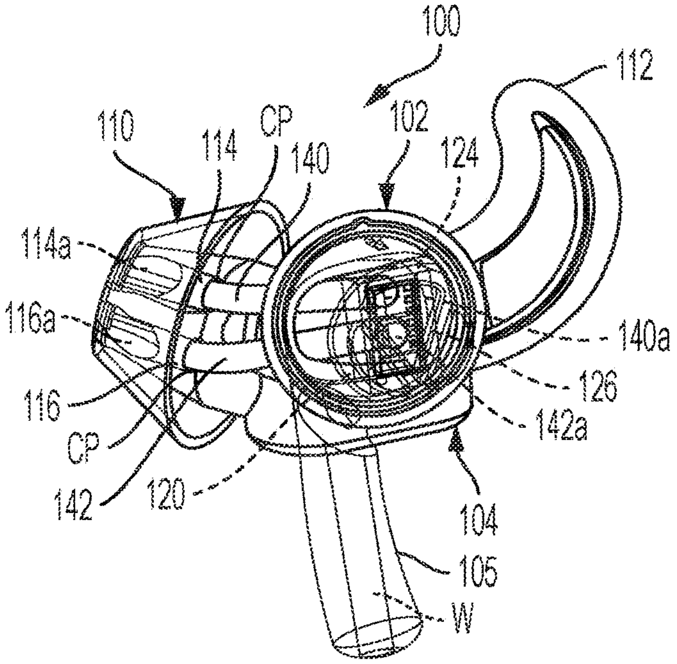
FIG. 3C illustrates the biometric monitoring device of FIG. 3B showing the ends of the light guides connected to the sensor module.

As illustrated in FIGS. 3B and 3C, a first light guide 140 is in optical communication, via a proximal end 140*a*, with an optical source 124 of the sensor module 120 and a second light guide 142 is in optical communication, via a proximal end 142*a*, with an optical detector 126 of the sensor module 120. The first and second light guides 140, 142 extend from the sensor module and through respective apertures 102*b* in the housing 102 and terminate at respective distal ends 140*b*, 142*b* (FIG. 5B). However, the light guides 140, 142 may extend though a common aperture in the housing 102 in other embodiments. In some embodiments, the housing 102 serves to support the light guides 140, 142.

The distal ends 140*b*, 142*b* of the light guides 140, 142 are configured to optically and physically couple with the respective free ends 114*b*, 116*b* of the flexible light guides 114, 116 when the body 104*a* of the ear gel module 104 is secured to the housing 102. The coupling point where the distal ends 140*b*, 142*b* of the light guides 140, 142 are optically and physically coupled with the respective free ends 114*b*, 116*b* of the flexible light guides 114, 116 is designated as CP in the figures.

The distal ends 140*b*, 142*b* of the light guides 140, 142 can be physically coupled with the respective free ends 114*b*, 116*b* of the flexible light guides 114, 116 in various ways. For example, the distal ends 140*b*, 142*b* of the light guides 140, 142 and the free ends 114*b*, 116*b* of the flexible light guides 114, 116 can be figured to have a "snap fit" connection. In other embodiments, the distal ends 140*b*, 142*b* of the light guides 140, 142 and the free ends 114*b*, 116*b* of the flexible light guides 114, 116 can be figured to have an insert fit (i.e., telescoping connection). For example, the distal ends 140*b*, 142*b* of the light guides 140, 142 can be configured to telescopically receive the free ends 114*b*, 116*b* of the flexible light guides 114, 116. Alternatively, the free ends 114*b*, 116*b* of the flexible light guides 114, 116 can be configured to telescopically receive the distal ends 140*b*, 142*b* of the light guides 140, 142 as illustrated in FIG. 3C.

In yet further embodiments, an adhesive may be utilized to physically couple the distal ends 140*b*, 142*b* of the light guides 140, 142 and the free ends 114*b*, 116*b* of the flexible light guides 114, 116. Furthermore, in some embodiments, the ear gel module 104 and housing 102 may be configured such that, when the ear gel module 104 is secured to the housing 102, the distal ends 140*b*, 142*b* of the light guides 140, 142 and the free ends 114*b*, 116*b* of the flexible light guides 114, 116 align to form a butt joint.

The distal ends 140*b*, 142*b* of the light guides 140, 142 and the free ends 114*b*, 116*b* of the flexible light guides 114, 116 may be configured to be removably secured to each other such that the ear gel module 104 can be replaced with another ear gel module 104.

The light guides 140, 142 and the flexible light guides 114, 116 physically couple to form a light transmission path and a light receiving path. By combining a respective light guide 140, 142 with a respective flexible light guide 114, 116, the respective properties of each allow for improved performance based upon the attributes of the sensor module 120 and the sensing region 10, as well as the attributes that define the distance between the sensor module 120 and the sensing region 10. According to some embodiments of the present invention, utilizing different materials to form the light guide path, i.e., a soft material for light guides 114, 116 and less flexible or rigid material for light guides 140, 142, are advantageous. The flexible and less flexible materials work in conjunction to provide the attributes necessary to facilitate contact with the skin, to promote comfort, and to reduce signal noise due to motion. Utilizing a less flexible material in the light guides 140, 142 facilitates the use of cladding to increase light transmission, and facilitates coupling to the optical source and detector of the sensor 120.

The flexible light guides 114, 116 may be formed from various types of conformable, light transmissive material, such as silicone. Other types of thermoplastic elastomers that are clear or transparent to a desired wavelength may be utilized, also. The light guides 140, 142 may be formed from various types of light transmissive material that are substantially rigid in nature (i.e., less flexible), such as polycarbonate, acrylic, silicone, glass, metal oxides, polyurethane, etc. The material of the flexible light guides 114, 116, and the material of the light guides 140, 142 is selected to be transparent to the respective wavelength of light emitted by the optical source 124 and received by the optical detector 126.

In some embodiments of the present invention, one or both of the flexible light guides 114, 116 and/or one or both to the light guides 140, 142 may have a generally cylindrical configuration. In other embodiments, one or both of the flexible light guides 114, 116 and/or one or both of the light guides 140, 142 may have a generally non-cylindrical configuration, e.g., rectangular, triangular, oval, etc.

In some embodiments, an optical filter may be integrated within one or more of the flexible light guides 114, 116 and/or one or more of the light guides 140 and 142. For example, a light guide 114, 116, 140, 142 may comprise a material having an optically filtering dye or a material which inherently filters one or more wavelengths of light. As one example, either or both of the flexible light guides 114, 116 and/or either or both of the light guides 140, 142 may comprise, wholly or partially, a dye therewithin. As one specific example, a dye, such as an infrared dye designed to block visible wavelengths but pass IR wavelengths may be utilized. For example, a polycarbonate or acrylic light guide, dyed with Filtron® absorptive dye E800 (Gentex Corporation, Carbondale, PA), would facilitate both light-guiding and IR-pass filtering functionality. Alternatively, another example of such an integrated physical optical filter comprises absorptive dyes available from Sabic (Riyadh, Saudi Arabia) dispersed in polycarbonate and/or acrylic to create an edge or long-pass optical filter. At least one of the light guides 114, 116, 140, 142 may be partially or wholly comprised of such a material, thereby facilitating the combinational purpose of light guiding and optical filtering. A few additional non-limiting examples of an inherently filtering material includes sapphire, which absorbs some infrared (IR) wavelengths, and glass, which absorbs some ultraviolet (UV) wavelengths. However, various types of filtering material may be utilized, without limitation.

In some embodiments, a physical optical filter can be disposed within the ear gel 110 at or near the location where the ends 114*a*, 116*a* of the flexible light guides 114, 116 are attached to the inner surface 110*b* of the ear gel 110.

In some embodiments, an optical filter may be integrated with the optical source 124 and/or the optical detector 126. For example, a bandpass filter, such as an interference filter or the like, may be disposed on the top of the optical source 124 and/or optical detector 126. Alternatively (or additionally), an optical filter effect may be integrated within the semiconductor material comprising the optical source 124 and/or optical detector 126, such as by selective ion implantation of certain regions within silicon or by band-gap engineering within compound semiconductors, such as the AlInGaAs or AlInGaN system of semiconductor engineering.

In some embodiments, one or both of the flexible light guides 114, 116 and/or one or both of the light guides 140, 142 may be surrounded or partially surrounded by a cladding/barrier material (114*c*, 116*c*, 140*c*, 142*c*) that is configured to at least partially block light from an external source from entering the light guides 114, 116,140, 142 at select locations along the light guides and/or at least partially confine light within the light guides 114, 116, 140, 142. The cladding/barrier material may be a light blocking material and/or a light reflective material and/or a material that has a higher optical scattering coefficient than the light guiding material of the light guides 114, 116, 140, 142. For example, the cladding material may be a dark (e.g., black, etc.) or silver (or other reflective color) coating, a material with refractive index that differs from the core light guide material. In some embodiments, the cladding material may be the supporting material itself (such as silicone or whatever the ear gel module 104 or housing 102 is formed from).

In some embodiments, the cladding material may be a reflective material between the light guides and the supporting material. In some cases the reflective material may surround the cylindrical portion of the light guides so that only the tips of the light guides are exposed to the light pathway. The reflective material may be mylar, metallic material, a roughened texture, or the like.

In some embodiments of the present invention, the light-guiding material of one or more of the flexible light guides 114, 116 and/or one or more of the light guides 140, 142 may comprise polarizing material. Exemplary polarizing material that can be used in accordance with embodiments of the present invention is available from American Polarizers, Inc., Reading, Pennsylvania, as well as Edmund Optics, Barrington, New Jersey.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A biometric monitoring device, comprising:

a housing;

an optical source positioned within the housing and configured to emit light;

an optical detector positioned within the housing and configured to detect a returned portion of the emitted light;

a first light guide extending from a first location on the housing and defined by a first material, wherein a first end of the first light guide is in optical communication with the optical source;

a second light guide extending from a second location on the housing and defined by the first material, wherein a first end of the second light guide is in optical communication with the optical detector;

an ear gel secured to the housing, defined by a second material having greater flexibility than the first material, and comprising:

a third light guide defined by the second material and comprising a first end optically coupled to a second end of the first light guide and secured to the ear gel;

a fourth light guide defined by the second material and comprising a first end optically coupled to a second end of the second light guide and secured to the ear gel; and an optical divider positioned between the third light guide and the fourth light guide and configured to prevent light from crossing between the third light guide and the fourth light guide.

2. The biometric monitoring device of claim 1, wherein the optical divider comprises a third material that is different from the second material.

3. The biometric monitoring device of claim 1, wherein the optical divider extends from an inner surface of the ear gel to an outer surface of the ear gel.

4. The biometric monitoring device of claim 1, wherein the first and second light guides are located external to the housing in adjacent spaced-apart relationship.

5. The biometric monitoring device of claim 1, wherein:
- the ear gel is removably secured to the housing;
- the second end of the third light guide is removably attached to the second end of the first light guide; and
- the second end of the fourth light guide is removably attached to the second end of the second light guide.

6. The biometric monitoring device of claim 1, wherein:
- the second end of the third light guide is positioned over at least a portion of the second end of the first light guide; and
- the second end of the fourth light guide is positioned over at least a portion of the second end of the second light guide.

7. The biometric monitoring device of claim 1, wherein the first and second light guides are substantially rigid.

8. The biometric monitoring device of claim 7, wherein the ear gel and the third and fourth light guides comprise a flexible optically transmissive material.

9. The biometric monitoring device of claim 1, wherein the ear gel further comprises a stabilizing member configured to engage a concha of a user.

10. The biometric monitoring device of claim 1, wherein the ear gel has a frusto-conical shape.

* * * * *